United States Patent [19]

Morales-George

[11] Patent Number: 4,656,997

[45] Date of Patent: Apr. 14, 1987

[54] DEVICE FOR TREATING ANATOMICAL PARTS

[76] Inventor: Hector Morales-George, 1170 Southwest 102 Ave., Miami, Fla. 33174

[21] Appl. No.: 620,312

[22] Filed: Jun. 13, 1984

[51] Int. Cl.$^4$ .............................................. A61B 19/00
[52] U.S. Cl. .................................... 128/1 R; 128/365; 4/601
[58] Field of Search ...................... 128/1 R, 365, 366; 604/903; 119/158, 159; 4/431, 601, DIG. 7

[56] References Cited

U.S. PATENT DOCUMENTS 3,867,906 2/1975 Johnson ............................... 119/158
4,510,889 4/1985 Jobe ..................................... 119/159

FOREIGN PATENT DOCUMENTS 2396504 3/1979 France ................................. 119/158
609516 6/1978 U.S.S.R. ............................... 119/158

Primary Examiner—Gene Mancene
Assistant Examiner—David I. Tarnoff
Attorney, Agent, or Firm—Robert T. Gammons

[57] ABSTRACT

A device for treating anatomical parts, particularly intestinal segments, in isolation comprising an open-ended chamber, a flexible diaphragm attached to one open end containing a plurality of incisions defining a opening through which the parts to be treated can be inserted into the chamber, a drain applied to the other end including a perforate strainer, a coupling element for connecting the drain to a source of vacuum and a plurality of nozzles positioned at equal distances abut peripherally of the chamber and substantially midway between the ends of the chamber through which a treating fluid can be ejected into the chamber.

1 Claim, 6 Drawing Figures

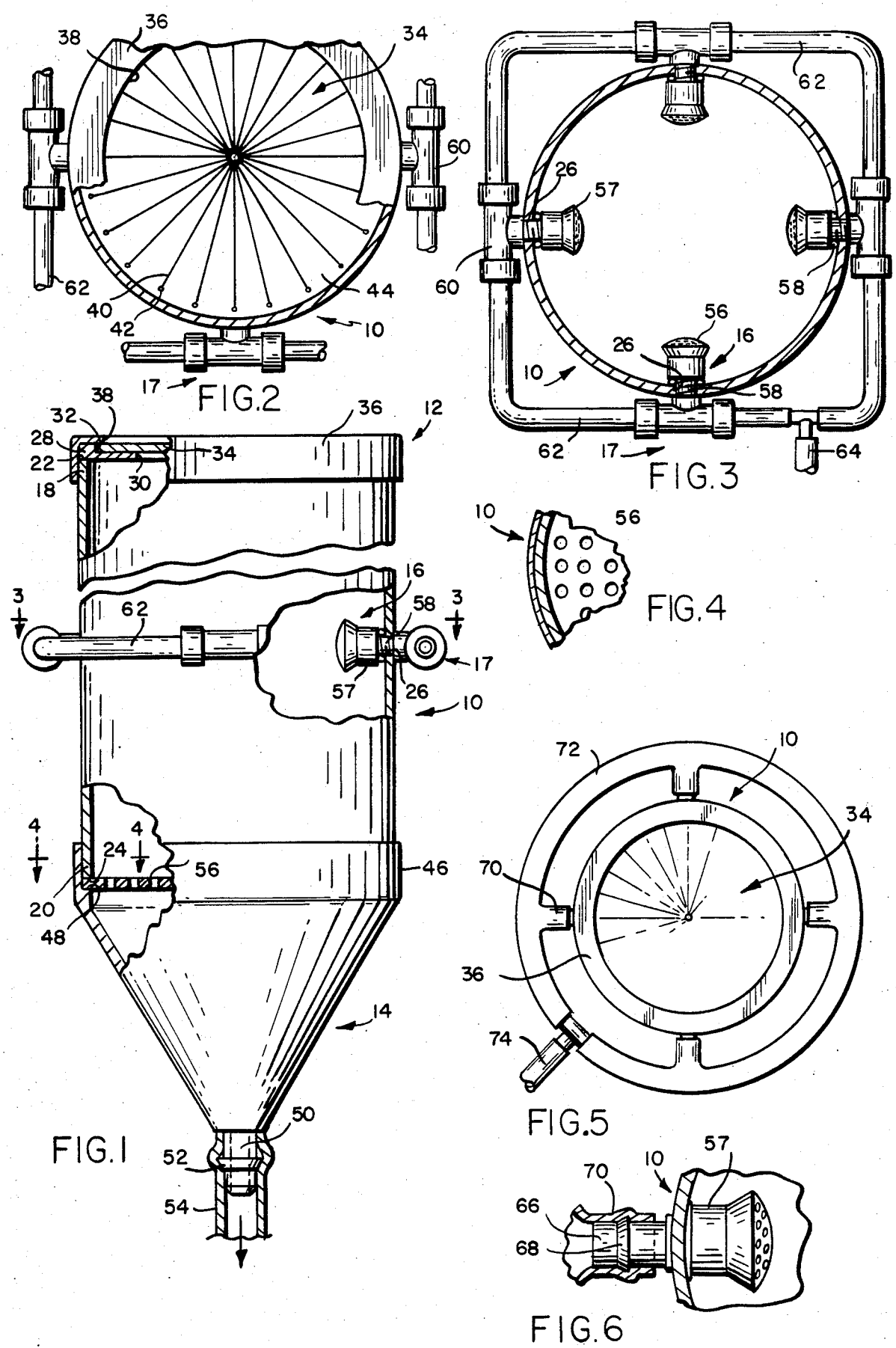

DEVICE FOR TREATING ANATOMICAL PARTS

BACKGROUND OF THE INVENTION

It is frequently necessary in surgery to subject swelled parts to decompression and cleaning, particularly in intestinal surgery and to do this in isolation to avoid the risk of abdominal contamination. All the known devices used for such purposes have the disadvantage of not providing for isolation of the part being treated. It is the purpose of this invention to provide a device which will enable isolating the affected part, for example, an intestinal segment, thereby to avoid potential contamination of the abdominal cavity, to decompress and clean the affected intestinal segment and to avoid the need for performing more than one surgical procedure to achieve the desired end.

SUMMARY OF THE INVENTION

As herein illustrated, the device comprises means defining an open-ended cylindrical chamber, a flexible diaphragm applied to one open end structured to permit the part to be treated to be introduced into the chamber, a drain applied to the opposite end embodying means defining a perforate strainer which subtends said open end of the chamber, a coupling element for connecting the drain to a source of vacuum and means for introducing a fluid into the chamber in the form of a spray at equally-spaced intervals peripherally thereof and substantially midway between the opposite ends of the chamber. The diaphragm desirably contains one or more incisions defining openings therethrough and, desirably, these incisions are peripherally-spaced radial cuts through the diaphragm intersecting at the geometrical center of the diaphragm. An annular cap dimensioned to fit over the end of the chamber is employed to clamp the diaphragm to the end of the chamber. The drain is a cone-shaped configuration, dimensioned at its base to fit over the end of the chamber against the strainer. Means for introducing fluid comprise a plurality of nozzle elements positioned radially within the chamber provided with nipples externally of the chamber connected to peripherally-positioned conductor means through which fluid is supplied to the chamber.

The invention will now be described in greater detail with reference to the accompanying drawings, wherein:

FIG. 1 is an elevation of the device with parts in section;

FIG. 2 is a fragmentary top view;

FIG. 3 is a section taken on the line 3—3 of FIG. 1;

FIG. 4 is a fragmentary section taken on the line 4—4 of FIG. 1;

FIG. 5 shows an alternative form of fluid system for introducing fluid into the device; and FIG. 6 is a fragmentary section of a nozzle and the plumbing coupling of FIG. 5.

Referring to the drawings, FIG. 1, the device as herein illustrated comprises a hollow cleaning chamber 10, at one end of which there is a closure 12 through which parts to be treated can be introduced into the chamber 10, a drain 14 at the opposite end connected to a vacuum source and a plurality of spray heads 16 and plumbing 17 therefor for introducing fluid into the chamber.

In a preferred form of the invention, the chamber 10 is of cylindrical cross section open at its opposite ends 18 and 20. The end 18 defines an annular face 22 and the end 20 defines an annular face 24. There are peripherally-disposed, equally-spaced openings 26 in the wall of the chamber substantially midway between the ends.

The closure 12 comprises a ring 28 corresponding in diameter to that of the end face 22 defining a through opening 30 concentric with the axis of the chamber and a recess 32 concentric with the opening 30, but of larger diameter. The closure 12 comprises, in addition, a diaphragm 34 corresponding in diameter to the recess 32 and in thickness to the depth of the recess 32 and a cap ring 36 dimensioned to fit over the end 18 of the chamber against the upper side of the ring 28 and the diaphragm 34 provided with an openings 38 concentric with the opening 30. The diaphragm 34 contains a plurality of radial incisions 40 spaced at equal peripheral distances from each other about the axis of the container and intersecting at the center thereof. Desirably, the outer ends of the incisions or slots 40 terminate in pierced holes 42. As thus structured, a plurality of triangular or pie-shaped segments 44 are provided which can be deflected downwardly by pressure applied to the upper face of the diaphragm to admit an object which is to be placed in the chamber, but which will return to their undeflected position when the pressure is released. The diaphragm desirably is of relatively stiff material so that it will be self-sustaining while, at the same time, being deflectable when pressure is applied perpendicular to the surface thereof.

The drain 14, as shown in FIG. 1, is of conical configuration and is provided at its base with a cylindrical flange 46 which defines an annular shoulder 48 corresponding in diameter to the end face 24 of the lower end 20 and which is internally dimensioned to slidingly fit over the lower end 20. At the apex, there is fixed a nipple 50 provided with a frustoconical rib 52 for force-fitting engagement with a flexible tube 54 which serves the combined function of providing for draining and evacuating the chamber 10. A perforated strainer plate 50 is positioned between the shoulder 48 and the face 24 and held clamped therebetween by application of the drain to the lower end of the cylinder.

The spray heads and plumbing 16,17 for introducing fluid into the chamber comprises in one form a plurality of spray heads 57 positioned internally of the chamber at a spacing corresponding to the openings 26, each of which is provided with a threaded nipple 58 which extends through the opening 26 and is screwed into a T coupling 60. There are four such spray heads and the four T couplings 60 to which they are connected. The plumbing 17 comprises pipes 62 connecting the T couplings and a pipe 64 connecting the pipes 62 to a source of fluid pressure. The T couplings 60 and the pipes 62 are comprised of plastic tubes.

Alternatively, as shown in FIGS. 5 and 6, the spray heads 56 are provided with smooth nipples 66 having frusoconical flanges 68 force-fitted into socket members 70 which are integrally formed along a length of plastic piping 72 which circumscribes the chamber and which is connected at the opposite ends to a flexible conductor 74.

In use, the part to be treated is removed from its situs by appropriate means, for example, forceps, and introduced into the chamber 10 through the diaphragm 34, whereupon a treating fluid which may be water or some solution which will have cleansing and/or decongesting properties is introduced into the chamber through the nozzles and suction is applied to the lower end of the chamber by way of the conductor 34. The process is continued until the part being treated is cleaned and restored to a healthy condition, whereupon the supply of fluid to the spray nozzles is cut off and the vacuum is cut off to permit removal of the part from the chamber.

The chamber and its component parts are desirably comprised of a plastic for ease in cleaning. Similarly, the nozzles may be comprised of plastic and the plumbing is comprised of plastic. The structure as described can be made inexpensively enough to be a throwaway item after one use, principally to insure against contamination.

The invention as herein illustrated includes the method of treating an afflicted part comprising incising the part, removing the incised part with the aid of forceps, depositing the incised part in an enclosure such as to isolate it from the ambient temperature, introducing a fluid into the enclosure to wash the afflicted part, evacuating the washing fluid and residuals flushed from the part, removing the part and restoring it to the situs from which it was removed by suturing.

It should be understood that the present disclosure is for the purpose of illustration only and includes all modifications or improvements which fall within the scope of the appended claims.

What is claimed is:

1. A device for treating anatomical parts in isolation comprising means defining an open-ended cylindrical chamber, a flexible diaphragm at one open end containing a plurality of peripherally-spaced radial incisions intersecting at the geometric center of the diaphragm, a rigid ring at said one open end of the chamber corresponding in diameter to said one open end of the chamber containing in one face a recess dimensioned to receive the diaphragm, a cap dimensioned to fit over said one open end of the chamber to clamp said ring and diaphragm to the chamber, a drain applied to the opposite end of the chamber embodying means defining a perforate strainer which subtends said opposite open end of the chamber, said drain being of conical configuration, a coupling element connected to the apex of the drain for connecting the drain to a source of low pressure and a plurality of nozzle elements for introducing fluid into the chamber substantially midway between the top and bottom, said nozzles being spaced equally about circumferentially of the chamber, said nozzle elements embodying nipples externally of the chamber and a conductor disposed peripherally of the chamber to which the nipples are connected.

* * * * *